June 27, 1967 J. W. PATTERSON Plant Pat. 2,749
NEW AND DISTINCT VARIETY OF ROSE
Filed March 3, 1966
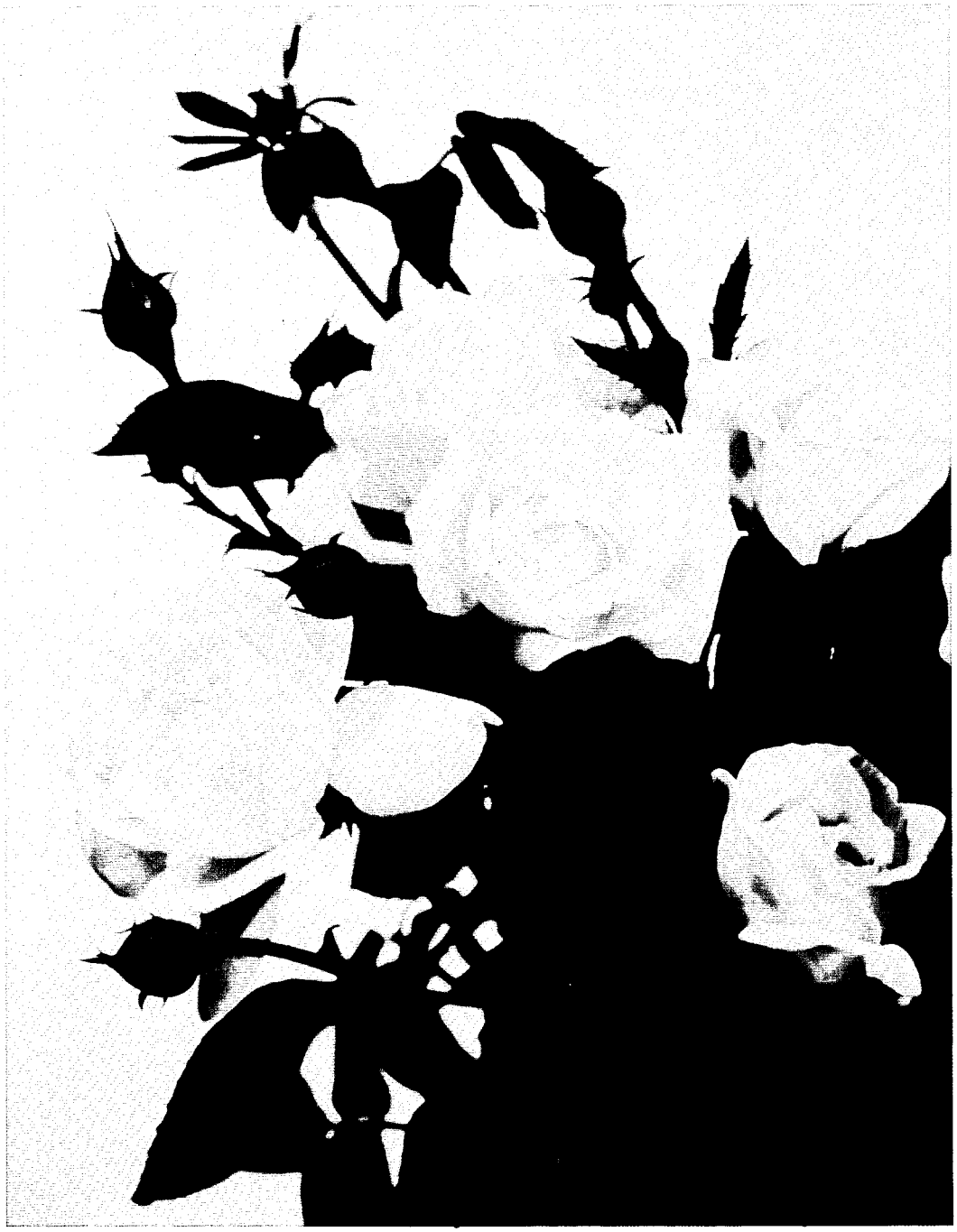

United States Patent Office

Plant Pat. 2,749
Patented June 27, 1967

2,749
NEW AND DISTINCT VARIETY OF ROSE

John W. Patterson, 6518 Kernel, Houston, Tex. 77017

Filed Mar. 3, 1966, Ser. No. 531,628
1 Claim. (Cl. Plt.—26)

The present invention relates to a new and distinct variety of rose plant of the floribunda class, which was originated by me by crossing the variety "Ma Perkins" (U.S. Plant Patent No. 1,143) with the variety "Pinocchio" (Plant Patent No. 484).

The primary objective in making this cross was to produce a new variety of rose plant with the hearty growth habits of the seed parent and to obtain a new and distinct blossom as to color and fragrance. It was also my purpose to achieve greater resistance of the new variety to mildew and other rose plant diseases. The objective was achieved, along with other desirable improvements, as evidenced by the following characteristics which are outstanding in the new variety and which distinguish it from its parents, as well as from all other varieties of which I am aware:

(1) Good growing and flower producing habits;
(2) Good flower fragrance;
(3) Beautiful delicate color of flowers;
(4) Good cut flowers; especially for corsages;
(5) Better than average disease resistance, particularly with respect to mildew and blackspot, as compared with other varieties grown under comparable cultural conditions at Houston, Tex.

In comparison with its seed parent "Ma Perkins," my new variety is definitely distinguished from this parent by its lower growth habits; it is more disease resistant; bears more blossoms, and the blossoms are more delicate in color and are more fragrant. The flowers are of better form in both the bud and open stages.

As compared with the pollen parent "Pinocchio" the new variety is a better grower, has larger blooms and is a more delightful color.

Asexual reproduction of my new variety by budding, as performed at Houston, Tex., Wills Point, Tex., and also at Tyler, Tex., shows that the foregoing characteristics and distinctions come true to form and are established and transmitted through succeeding propagations.

The accompanying drawing shows typical specimens of the vegetative growth and flowers of my new variety in different stages of development and as depicted in color as nearly true as it is reasonably possible to make the same in a color illustration of this character.

The following is a detailed description of the new variety, with color terminology in accordance with Horticultural Colour Chart of the Royal Horticultural Society:

Type: Bush; outdoor; seedling; for garden decoration.
Class: Floribunda.
Breeding: Seedling.
Seed parent.—"Ma Perkins."
Pollen parent.—"Pinocchio."
Propagation: Holds its distinguishing characteristics through succeeding propagations by budding.

*Flower*

Locality where grown and observed: Houston, Tex.; also Wills Point, Tex.
Flowers borne: Usually several to stem. Clusters on strong, medium length stems.
Quantity of bloom: Free to abundant, outdoors.
Continuity: Continuous during growth season.
Fragrance: Moderate. Nature—tea.

Bud:
*Peduncle.*—Medium length, average caliper; entirely smooth; no prickles.
*Color.*—Scheeles Green, Plate 860/3, page 175.
*Before calyx breaks.*—Size—medium. Form—medium length; ovoid; with very few cilia on surface of bud.
*As calyx breaks.*—Color—near Claret Rose, Plate 21/2 and Plate 21/1, page 21.
*As first petal opens.*—Size—medium length; ovoid. Color: outside—upper ½ and edge of petal, Crimson, Plate 22/3, page 22; lower ½ petal and base of petal Dawn Pink, Plate 532/2, page 137; inside—Dawn Pink, Plate 523/1, page 137.
*Opening.*—Opens up well.

Bloom:
*Size (when fully open).*—Medium, 3 inches.
*Petalage.*—Double, 35 to 40 petals, arranged regularly.
*Form.*—High centered.

Petals: Medium thickness; with both inside and outside satiny. Shape: outer—obovate; intermediate—obovate; inner—obovate.

This description of a newly-opened flower was made from a rose grown outdoors in the month of October at Houston, Tex.

*Color.*—Outside petal: outside surface—top rim of petal—Spinel Pink, Plate 0625/2, page 184, shading to lighter color Venetian Pink, Plate 420/2, page 125; slight trace of Mimosa Yellow, Plate 602/3, page 143, showing at base; inside surface—upper ½ petal—Spinel Pink, Plate 0625/2, page 184; with lower ½ petal, Venetian Pink, Plate 420/1, page 125, slight trace of Mimosa Yellow, Plate 602/3, page 143, at base. Inner petal: outside surface—Spinel Pink, Plate 0625/2, page 184, base of petal Mimosa Yellow, Plate 602/2, page 143; inside surface—Venetian Pink, Plate 420, page 125, base of petal Mimosa Yellow, Plate 602/2, page 143.

This description was made from a rose that was open for 3 days outdoors in the month of October, at Houston, Tex.

*Color.*—Outside petal: outside surface—Rose Pink, Plate 427/1, page 126, shading to Rose Pink, Plate 427/2, page 126, to Rose Pink, Plate 427/3, page 126; inside surface—Spinel Pink, Plate 0625/3, page 184, base of petal near white. Inner petal: outside surface—Rose Pink, Plate 427/2 shading to Rose Pink, Plate 427/3, page 126, tip of base Sulphur Yellow, Plate 1/3, page 1.
*General color effect.*—Newly-opened flower—outer edge of petals Spinel Pink, Plate 0625/2, page 184, shading to Venetian Pink, Plate 420, page 125 in center. 3-days open—outer tips of petals Rose Pink, Plate 427/1, page 126, shading to Rose Pink, Plate 427/3, page 126, to almost white at center of flower.
*Behavior.*—Drop off cleanly; color heightened in warm spring and autumn. Takes hot weather well also.
*Flower longevity.*—On bush in garden—4 to 5 days in October. Cut roses grown outdoors and kept at living-room temperatures 4 to 5 days. Also lasts well for corsages.

*Reproductive organs*

Stamens: Many; arranged regularly about pistils.
Filaments: Medium length; most with anthers. Color—Sulphur Yellow, Plate 1/1, page 1.

Anthers: Open at various times; medium size. Color—Indian Yellow, Plate 6/2, page 6.
Pollen: Moderate; color—Cadmium Orange.
Pistils: Average number.
Styles: Short; medium caliper, bunched.
Stigma: Color—Indian Yellow, Plate 6/3, page 6.
Hips: Some; average length, ovoid; smooth.
Sepals: Permanent; short, spear shaped. Color: inside—Scheeles Green, Plate 860/3, page 175, slightly overlaid with Erythrite Red, Plate 0027/1, page 190; outside—Scheeles Green, Plate 860/2, page 175, slightly edged and streaked with Erythrite Red, Plate 0027, page 190.
Seeds: Average number, small, from 10 to 25 in number.

*Plant*

Foliage:

*Leaves.*—Compound of usually 5 to 7 leaflets; abundant; medium size; glossy.

*Leaflets.*—Shape—ovoid. Apex — obtuse. Base—round. Margin—serrate.

*Color.*—Mature: upper surface— near Spinach Green, Plate 0960, page 187; under surface—near Spinach Green, Plate 0960/1, page 187. Young: upper surface—Scheeles Green, Plate 860, page 175, with veins and outside rim Garnet Lake, Plate 828, page 72; underside surface—Spinach Green, Plate 0960/1, page 187, slightly overlaid with Garnet Lake, Plate 828/2, page 172.

*Rachis (the supporting stem of the compound leaf).*—Medium caliper. Upper side—grooved. Under side—few prickles.

*Stipules.*—Length—short; narrow with points turning out at an angle less than 45°.

Growth:

*Habit.*—Bush; compact.

*Growth.*—Vigorous.

*Canes.*—Medium caliper.

*Main stems.*—Color—Spinach Green, Plate 0960/3, page 187, with occasional Indian Lake, Plate 826/1, page 17, showing on one side. Prickles: color—near Garnet Brown, Plate 00918/3, page 192. Few thorns.

*Branches.*—Color—near Scheeles Green, Plate 860, page 175. Thorns—few: Prickles—few; color—near Orange Buff, Plate 507/1, page 133. Hairs—none.

*New shoots.*—Color—Scheeles Green, Plate 860/3, page 175. Prickles—few; color—near Erythrite Red, Plate 0027, page 190. Hairs—none.

I claim:

A new and distinct variety rose plant of the floribunda class, substantially as herein shown and described, characterized particularly as to novelty by the unique combination of good growing and flower producing habits, abundant glossy green foliage, medium size flowers which are borne on strong stems of medium length, mostly in clusters, good flower form, good flower fragrance, better than average disease resistance, particularly with respect to mildew and blackspot, and attractive color tonality of the flowers corresponding to Spinel, Venetian and Rose Pink.

No references cited.

ANTONIO F. GUIDA, *Acting Primary Examiner.*

ROBERT E. BAGWILL, ABRAHAM G. STONE, *Examiners.*